(12) United States Patent
Ling (10) Patent No.: US 9,987,140 B2
(45) Date of Patent: Jun. 5, 2018

(54) DYNAMIC FORCE GENERATION FOR BONE REPAIR

(71) Applicant: Mechano-Transducton, LLC, St. Paul, MN (US)

(72) Inventor: Jeremy John Ling, St. Paul, MN (US)

(73) Assignee: Mechano-Transduction, LLC, St. Paul, MN (US)

( * ) Notice: Subject to any disclaimer, the term of this patent is extended or adjusted under 35 U.S.C. 154(b) by 35 days.

(21) Appl. No.: 14/771,633

(22) PCT Filed: Mar. 3, 2014

(86) PCT No.: PCT/US2014/019924
§ 371 (c)(1),
(2) Date: Aug. 31, 2015

(87) PCT Pub. No.: WO2014/137909
PCT Pub. Date: Sep. 12, 2014

(65) Prior Publication Data
US 2016/0015525 A1      Jan. 21, 2016

Related U.S. Application Data

(60) Provisional application No. 61/851,230, filed on Mar. 4, 2013.

(51) Int. Cl.
*A61B 17/70* (2006.01)
*A61F 2/44* (2006.01)
(Continued)

(52) U.S. Cl.
CPC ............ *A61F 2/4455* (2013.01); *A61B 17/70* (2013.01); *A61B 17/7016* (2013.01);
(Continued)

(58) Field of Classification Search
CPC .......................... A61B 17/72; A61B 17/7225
See application file for complete search history.

(56) References Cited

U.S. PATENT DOCUMENTS 5,127,913 A * 7/1992 Thomas, Jr. ....... A61B 17/1707
606/62
5,191,880 A    3/1993 McLeod et al.
(Continued)

FOREIGN PATENT DOCUMENTS

| CH | 618 610 A5 | 8/1980 |
| CN | 102905625 A | 1/2013 |
| WO | 2011029021 A2 | 3/2011 |

OTHER PUBLICATIONS

International Search Report for corresponding International Patent Application No. PCT/US2014/019924 dated Jun. 20, 2014.

*Primary Examiner* — Ellen C Hammond
(74) *Attorney, Agent, or Firm* — Merchant & Gould P.C.

(57) ABSTRACT

An orthopedic device delivers dynamic forces to a desired remote bone region. Dynamically arranged mechanical forces are known to stimulate bone cells (the process of mechanotransduction). The device includes an implantable element configured to couple with a generally accessible and healthy bone area, from which location it's configured to transmit forces to a remote bone area in need of repair, regrowth, or regeneration. Further, the device positions and orients the implantable element where it can be readily acted on by the device's force generator. The force generator is configured to impart dynamic forces that are transmitted through the implantable element and into a desired bone mass including a remote bone area in need of repair. This device promotes fracture healing, treats osteoporotic or other poor quality bone, and promotes vertebral fusion in conjunction with a spinal fusion procedure.

15 Claims, 9 Drawing Sheets

(51) Int. Cl.
    *A61F 2/28*     (2006.01)
    *A61B 17/86*     (2006.01)
    *A61B 17/72*     (2006.01)
    *A61F 2/30*     (2006.01)
    *A61B 17/00*     (2006.01)
    *A61B 17/80*     (2006.01)

(52) U.S. Cl.
    CPC .......... *A61B 17/72* (2013.01); *A61B 17/7225* (2013.01); *A61B 17/80* (2013.01); *A61B 17/866* (2013.01); *A61F 2/28* (2013.01); *A61B 17/8004* (2013.01); *A61B 2017/00876* (2013.01); *A61F 2002/286* (2013.01); *A61F 2002/30079* (2013.01); *A61F 2002/30668* (2013.01)

(56) References Cited

U.S. PATENT DOCUMENTS

| | | |
|---|---|---|
| 5,269,745 A | 12/1993 | Liboff et al. |
| 5,376,065 A | 12/1994 | McLeod et al. |
| 5,458,558 A | 10/1995 | Liboff et al. |
| 5,518,496 A | 5/1996 | McLeod et al. |
| 6,022,349 A | 2/2000 | McLeod et al. |
| 6,032,677 A | 3/2000 | Blechman et al. |
| 6,387,096 B1 | 5/2002 | Hyde, Jr. |
| 6,678,562 B1 | 1/2004 | Tepper et al. |
| 6,932,818 B2 | 8/2005 | Behrens |
| 7,108,663 B2 | 9/2006 | Talish et al. |
| 8,114,036 B2 | 2/2012 | Krompasick |
| 8,277,402 B2 | 10/2012 | Chisena et al. |
| 2005/0043659 A1 | 2/2005 | Challis et al. |
| 2008/0086135 A1* | 4/2008 | White ................ A61B 17/7059 606/246 |
| 2011/0130794 A1 | 6/2011 | Vaidya |
| 2012/0101361 A1 | 4/2012 | Rains et al. |
| 2012/0316482 A1 | 12/2012 | Karim |
| 2012/0330091 A1 | 12/2012 | Chisena et al. |
| 2013/0165733 A1* | 6/2013 | Rogachefsky ......... A61N 2/008 600/12 |

* cited by examiner

DYNAMIC FORCE GENERATION FOR BONE REPAIR

This application is a National Stage Patent Application of PCT/US2014/019924, filed Mar. 3, 2014, which claims benefit of U.S. Provisional Patent Application No. 61/851,230, filed Mar. 4, 2013 and which applications are incorporated herein by reference. To the extent appropriate, a claim of priority is made to each of the above disclosed applications.

BACKGROUND

Wolff's Law states that bone grows and remodels in response to the forces that are placed upon it. Throughout life bone is constantly remodeled by the coordinated action of bone-resorbing osteoclasts and bone-forming osteoblasts in basic multicellular units. This continuous remodeling likely serves to prevent and remove fatigue-related microdamage and allows adaptation of the bone mass and structure. In a musculoskeletal system, the biomechanical environment plays a key role in repairing, maintaining, and remodeling of bone to meet its functional demands. After injury to bone, placing specific forces, in specific therapy frequencies can stimulate and accelerate the natural bone repair process to help the bone remodel and become healthy, normal bone again.

For several decades, clinicians and researchers have been investigating the relationship between the mechanical environment near bone repair sites and the speed of secondary bone healing. A growing body of evidence derived from animal models and clinical trials now suggests that dynamic forces can be key in promoting and accelerating the bone repair process. Certainly, the ability to promote and speed the rate of bone healing would provide significant benefits to patients and the healthcare industry in general. Approximately six million extremity fractures occur each year in the United States. Five to ten percent of these fractures will go on to delayed or non-union fractures, adding further burden to the healthcare system. Spinal fusion is surgery to permanently connect two or more vertebrae in your spine, eliminating motion between them. Spinal fusion involves techniques designed to mimic the normal healing process of broken bones. During spinal fusion, bone or a bone-like material is placed within the disc space between two vertebral bodies to fuse the vertebral levels together into a single bony element. Delayed or non-union fractures are even more common in spinal fusion procedures, with some reports suggesting up to a third of these cases don't adequately fuse. There are also various other conditions in which osteoporotic or poor quality bone becomes subject to fractures, deformities, and/or heals slowly. In the aforementioned conditions of fracture healing, vertebral fusion, and/or osteoporotic/poor quality bone, patients and healthcare providers alike are relying on a successful bone repair process to occur. However the natural bone repair process isn't always successful, and often proceeds at an excessively slow rate. Evidence suggests dynamic forces can be applied to injured bone regions to stimulate and accelerate the bone repair process.

There is an existing class of medical devices referred to as bone stimulators. They are tools that aid in bone healing and recovery, especially in the instance of delayed or non-union. The technology behind the bone stimulators is summarized into five main groups based on modes of action. These types are summarized in Table 1 below.

TABLE 1

| | Types-Bone Stimulators | Mode of Action |
|---|---|---|
| 1 | Inductive | A wire coil that creates an electromagnetic field. |
| 2 | Direct Current | A power source delivers a constant current to the desired site. |
| 3 | Capacitive | An electrical field generated between two electrodes placed at opposite ends of the treatment site. |
| 4 | Magnetic | Low energy magnetic fields applied either statically or dynamically (pulsed) |
| 5 | Ultrasonic | Low intensity, pulsed ultrasonic signal to fracture site. |

Figure 1:
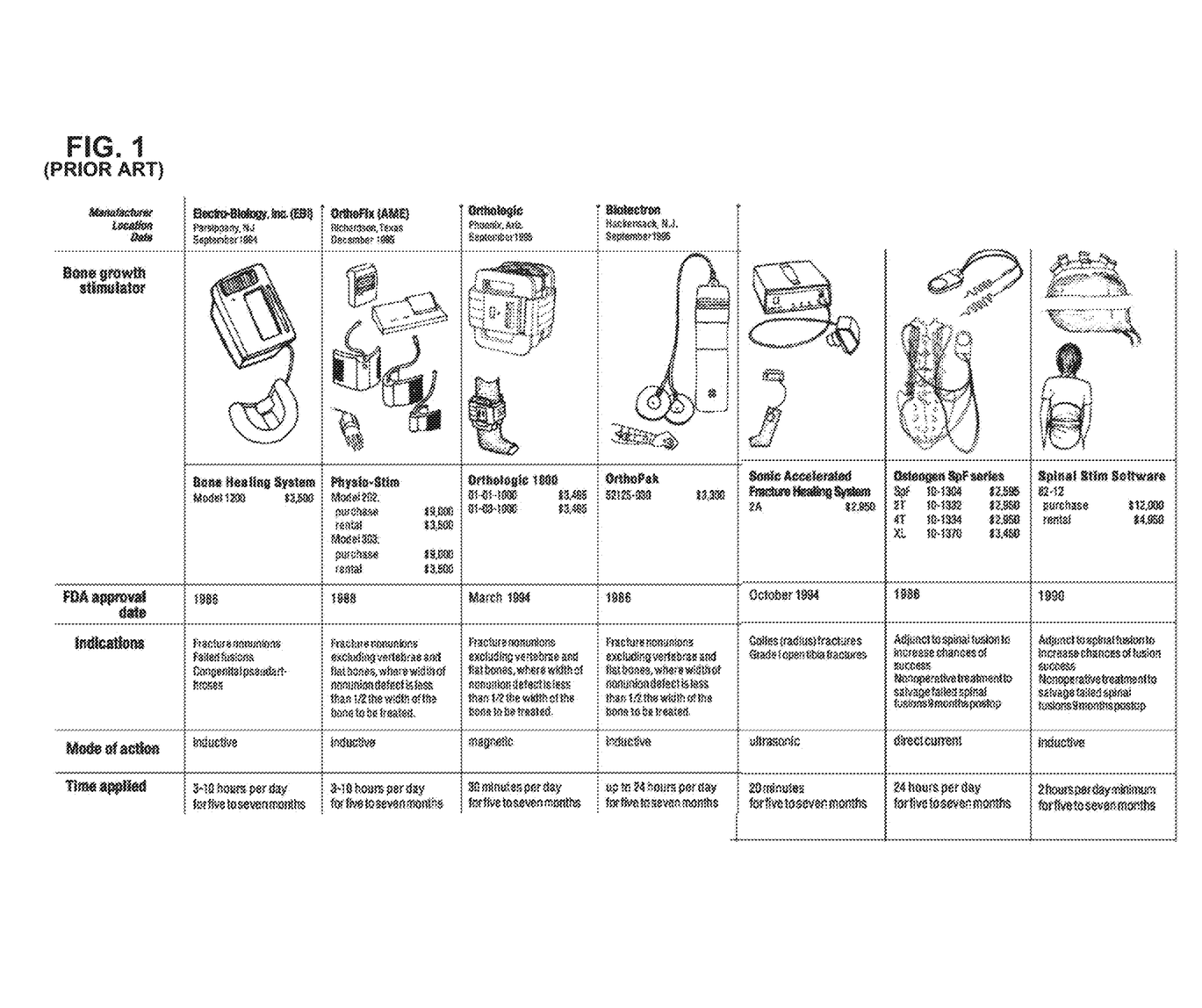
FIG. 1: A table illustrating a number of commercial marketed bone stimulator devices.

Table 2 shown in FIG. 1 illustrates some commercial marketed bone stimulator devices. These technologies are intended to reduce incidence of delayed or non-union fractures and/or fusion, improve the rate of bone healing, and shorten fracture healing times. These are typically home health care devices, in which the patient is trained how to operate and administer the device. None of these commercial embodiments are utilizing dynamic force delivery to stimulate bone repair. Furthermore, the existing bone stimulators are expensive devices, often costing several thousands of dollars. It would be beneficial to the healthcare industry to provide a lower cost approach to stimulating the bone repair process.

The existing commercial art is utilizing electrical, magnetic, and ultrasonic modes to stimulate bone cells. These modes of action are favorable in that they typically can be delivered non-invasively. For example, ultrasound signals, electrical signals, and magnetic fields are known to readily penetrate human tissue. In this manner, the bone stimulator devices can be placed in the general vicinity of the desired bone region, and the stimulator signal can penetrate into the body. However, as previously summarized, there is a large body of evidence suggesting dynamic forces (not electrical, magnetic, or ultrasonic signals) are key ingredients in stimulating bone repair and growth. The existing types of bone stimulators are not utilizing dynamic forces as a mode of action.

There are various challenges in delivering dynamic forces to a desired bone region. For example, typically it is best to apply forces directly to the bone. Challis et al. in U.S. Patent Publication No. 2005/0043659 A1 discloses a pressure cuff that non-invasively delivers compressive forces to a desired lone bone extremity. Research has shown that the magnitude and frequency of the force application must be finely controlled to aid the bone repair process. Too much force can be detrimental to bone repair, and too little will not stimulate the repair process. Non-invasive approaches like Challis must contend with delivery through a wide array of soft tissues, with huge variability patient to patient. This makes it nearly impossible to finely control the final force magnitude that actually reaches the desired bone area. Therefore, applying forces by directly coupling to the bone region in need of repair is a preferred embodiment for appropriate control of force delivery. However, various scenarios exist where it is not possible to directly couple to a bone region in need of repair or growth. Often the injury itself makes it prohibitive to directly stimulate to the injured bone. For example, in the instance of bone fractures, because of the trauma, inflammation, and subsequent cellular healing activities occurring at the fracture site, directly coupling to the fracture site would be difficult, painful, and disruptive to the cellular healing process. In the instance of vertebral fusion, the bone repair site is sealed within the vertebral disc space. Therefore it is not feasible, without extreme complexity and risk, to directly couple to the bone repair region within the disc space. In the instance of osteoporotic or poor quality bone, the bone integrity may no be adequate for directly coupling the force delivery apparatus.

Furthermore, in addition to the challenges of directly coupling to a bone region in need of repair, there are further challenges in transmitting the appropriate dynamic forces into a desired bone region in need of repair. Various scenarios may exist where the location, access constraints, or other anatomical obstacles within the body can prohibit force transmission to a desired remote bone region in need of repair. There is also research evidence that suggests, in addition to the magnitude and frequency of dynamic force application, the direction of force application to the injured bone is also an important variable for stimulating bone repair. For example, in the instance of bone fractures, forces that generally compress the fracture site are thought to be more beneficial than forces that shear the fracture site.

There is a large body of scientific and clinical evidence suggesting dynamic forces are key ingredients in stimulating bone repair and growth. Existing commercial art has not focused on force delivery to a desired bone area; rather existing art is utilizing electrical, magnetic, and ultrasonic modes to stimulate bone cells. Dynamic force delivery to a desired bone region could be utilized, for example, to promote fracture healing, treat osteoporotic or other poor quality bone, and promote vertebral fusion in conjunction with a spinal fusion procedure. There are various challenges in directly coupling to a bone region in need of repair. There are also various challenges in transmitting forces into the bone region in need of repair. Despite the challenges, there is a large body of evidence suggesting it would be beneficial to develop new art that focuses on delivering force stimulation to remote bone areas in need of repair. Furthermore, it would be beneficial to accomplish such an orthopedic apparatus in a simple cost effective manner, and thereby allow the technology to be applied as a cost savings adjunct, rather than an expensive secondary treatment option.

SUMMARY OF THE INVENTION

The present inventor has recognized, among other things, that there exists a need for an orthopedic apparatus that delivers dynamic forces to a desired bone region in need of repair.

In some embodiments, an apparatus for delivering dynamic forces to a desired bone region includes an implantable element that rigidly couples to a generally healthy region of a bone mass which includes a remote bone region in need of repair. The implantable element is made of, or includes, a magnetic material. The magnetic material is positioned and oriented to influence the magnitude and direction of force application to the bone region in need of repair. A non-implantable external force generator is configured to align with the implantable element and operate to impart forces that are transmitted through the implantable element to the remote bone region in need of repair. In some embodiments, the external force generator is configured to impart a dynamic magnetic field on the implantable element. The dynamic magnetic field induces forces on the magnetic material of the implantable element. Those forces are transmitted through the implantable element to the remote bone region in need of repair.

In some embodiments, the external force generator includes a permanent magnet configured for motion. The motion of the permanent magnet generates a dynamic magnetic field, which in turn imparts forces on the implantable element. In some embodiments, the external force generator also includes a multiphase winding commutated by drive circuitry, wherein the permanent magnet acts as a single pole rotor whose motion is initiated and controlled by the windings and drive circuitry. In some embodiments, the external force generator also includes features to align and orient the magnetic field with respect to the implantable element. Such alignment provisions enable the apparatus to control the magnitude and direction of forces applied to the injured bone region.

In some embodiments, at least a portion of the implantable element is positioned subcutaneously. Wherein the subcutaneous positioning minimizes the distance between the implantable element and the external force generator. Wherein the subcutaneous positioning may also allow the implantable element to be palpated through the soft tissues to assist in locating and aligning with the implantable element. In some embodiments, the external force generator includes features that compress the soft tissue around the implantable element to further reduce the distance between the implantable element and the external force generator and facilitate alignment of the apparatus.

This summary is intended to be an overview of subject matter of the present patent application. It is not intended to provide an exclusive or exhaustive explanation of the invention. The detailed description is included to provide further information about the present patent application.

DESCRIPTION OF THE DRAWINGS

Drawings of some embodiments of the apparatus are included to assist in explaining the basic inventive ideas. These drawings are intended as illustrations and are not meant to limit the invention described herein.

DETAILED DESCRIPTION

The subject matter described herein may take form in a variety of embodiments, including but not limited to, the embodiments, components, arrangements of components, assembly methods and arrangements of methods, and apparatus usage procedures, and arrangements of procedures as described below. The embodiments described, while possibly being preferred embodiments, are illustrative examples and are not meant to limit the invention described herein.

Figures 1A, 1B:
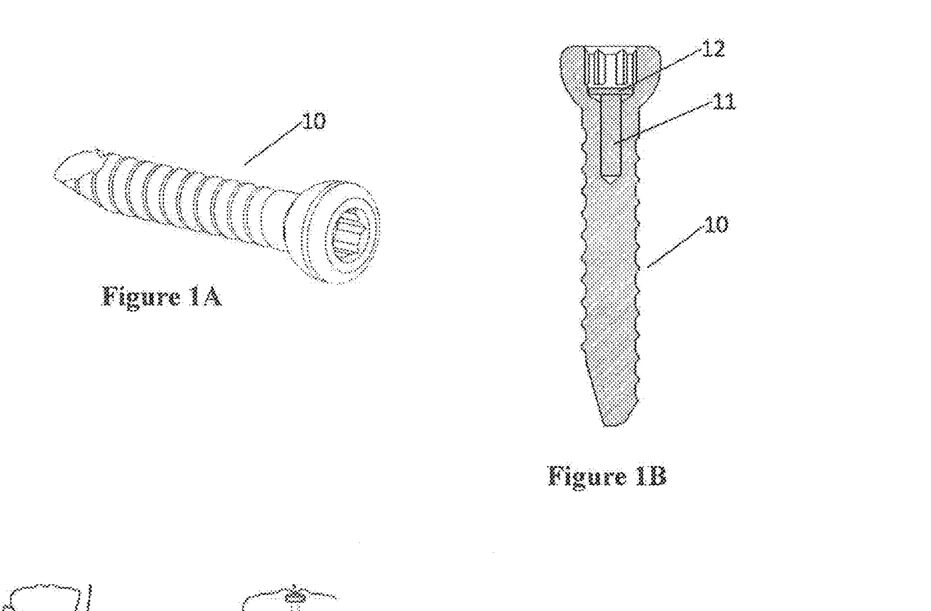
FIG. 1A: A perspective view of an implantable element for coupling with a bone mass.
FIG. 1B: A section view of an implantable element including a magnetic material.

The apparatus includes an implantable element configured for direct attachment to a bone mass. Some examples of existing components that could serve as the implantable element include bone pins, bone screws, bone plates, intramedullary rods, spinal fusion rods, pedicle screws or any other implant grade device approved for direct contact with bone. Alternatively, the implantable element could take form in new custom arrangements suitable for direct attachment to a bone mass. In FIG. 1A the implantable element is illustrated as a bone screw 10. Bone screws of this type are commonly used to stabilize fractures and/or secure implants such as plates or rods. The apparatus requires that the implantable element include magnetic properties. In FIG. 1A for example, the bone screw 10 could be fabricated from a magnetic grade stainless steel. Most implantable grade materials however are not magnetic. FIG. 1B illustrates an embodiment of a bone screw that includes a magnetic material 11 captured within the screw body. Since magnetic materials are generally not biocompatible, this embodiment traps and seals the magnetic material 11 within the screw body. A cavity cover 12, fabricated from an implantable grade biocompatible material, can be utilized to hermetically seal the magnetic material 11 to and/or within the implantable element. The magnetic material 11, for example could be iron, nickel, cobalt or various other materials with magnetic properties. In another embodiment a permanent magnet could also be used as the magnetic material. In this manner, a bone screw fabricated from the typically used implant grade materials, for example non-magnetic stainless steel or titanium, could contain a magnet material embedded and sealed within its body, so as to present no biocompatibility concerns. Bone screws are common to many orthopedic repair procedures, and therefore could provide convenient, practical means for delivering forces to various areas of the skeletal frame. Furthermore, bone screws also can be safely removed at a later time. For example in some instances it may be specifically desirable to remove the magnetic bone screw for MRI compatibility. In alternative embodiments, a, similar approach of embedding and sealing a magnetic material within an implantable element could take form in components such as bone pins, bone plates, intramedullary rods, pedicle screws, and transverse connectors.

Figure 2:
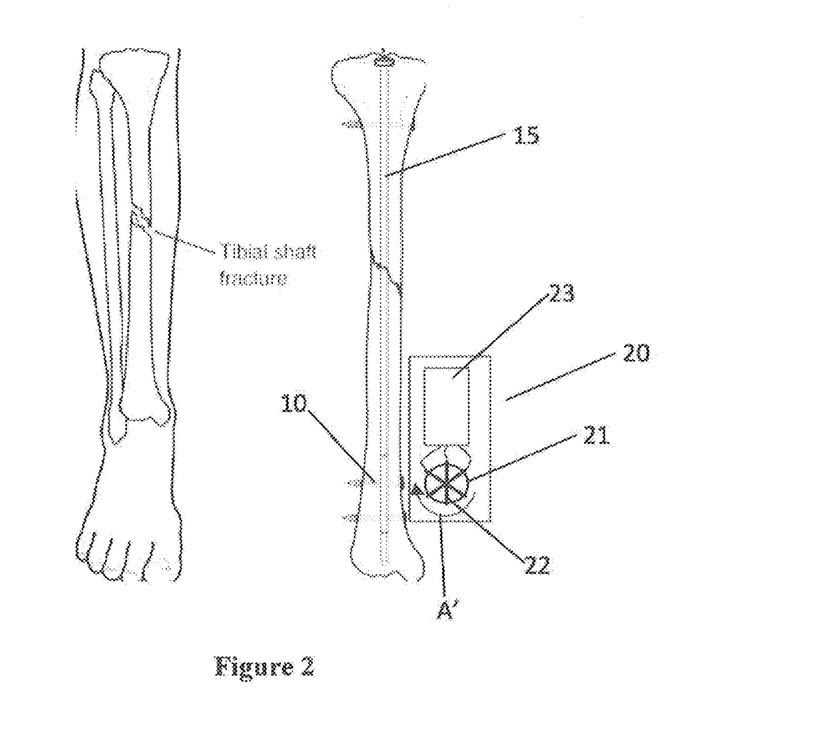
FIG. 2: An anterior view of a tibia fracture in conjunction with the force delivery apparatus.

The apparatus also includes an external force generator that can be worn or placed externally in the vicinity of the implantable element. When the apparatus is activated, the force generator operates in cooperation with the implantable element to transmit forces into a desired bone mass. FIG. 2 illustrates a tibial shaft fracture stabilized by an intramedullary rod 15. The apparatus delivers dynamic forces to the fracture site to stimulate and accelerate the repair process.

As illustrated in FIG. 2, an external force generator 20 includes a permanent magnet 21 configured for movement A'. Permanent magnet 21 is surrounded by windings 22. Drive electronics 23 commutate the windings to induce rotational movement of the permanent magnet 21. In this manner, the permanent magnet acts as its own motor, rather than requiring some form of additional driver/motor hardware to initiate magnet motion. As the permanent magnet moves, it imparts a dynamic magnetic field on the magnetic material in the bone screw 10, whereby forces are generated and transmitted into the bone mass. In FIG. 2, the forces are transmitted through bone screw 10 to the remote fracture site.

The force generator 20 embodiment illustrated in FIG. 2 is a unique design. For home health care scenarios where the patient is operating the apparatus to administer force therapy, it's important to have a cost effective, small, portable, and easy to operate architecture, among other things. Furthermore, the existing classes of bone stimulators are indicated as a secondary treatment option, for a bone injury that is not healing properly on its own. This indication is, in part, due to the excessive cost of the devices. The inventive nature of the FIG. 2 embodiment is partially aimed at cost efficiency to enable prescription of the technology as part of the mainline bone repair treatment. The modern healthcare environment requires, in general, that new devices present cost savings opportunities to reduce the overall burden on the health care industry. The force generator embodiment in FIG. 2 is an inventively simple design that includes basic motor drive electronics, magnet wire wrapped around a permanent magnet to create windings, and an enclosure to contain the components and orient the force delivery.

Figure 3A:
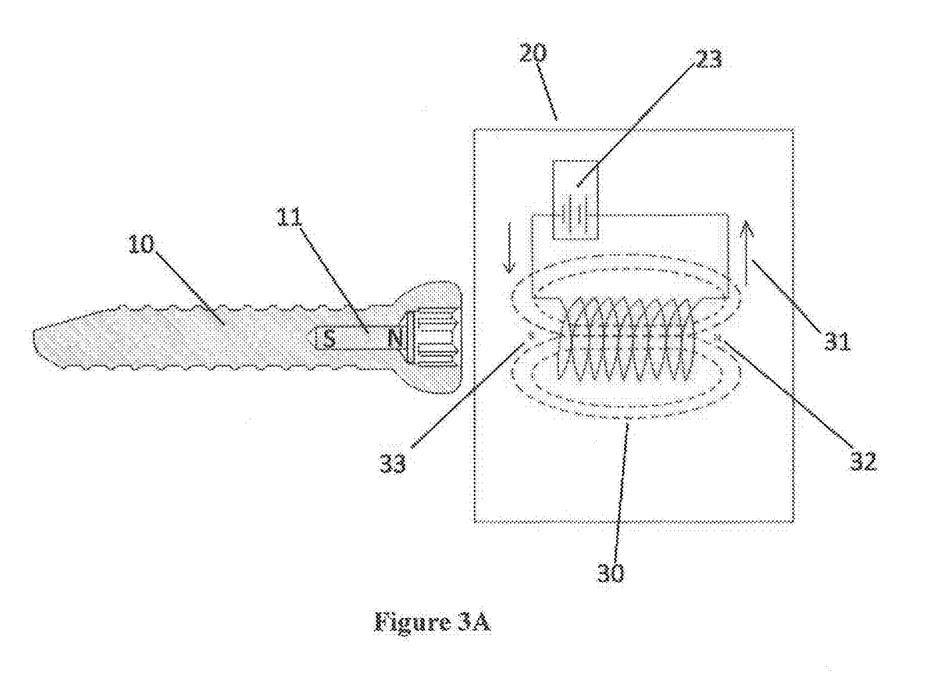
FIG. 3A: An external force generator in the form of an electro-magnet for imparting a dynamic force on an implantable element.
Figure 3B:
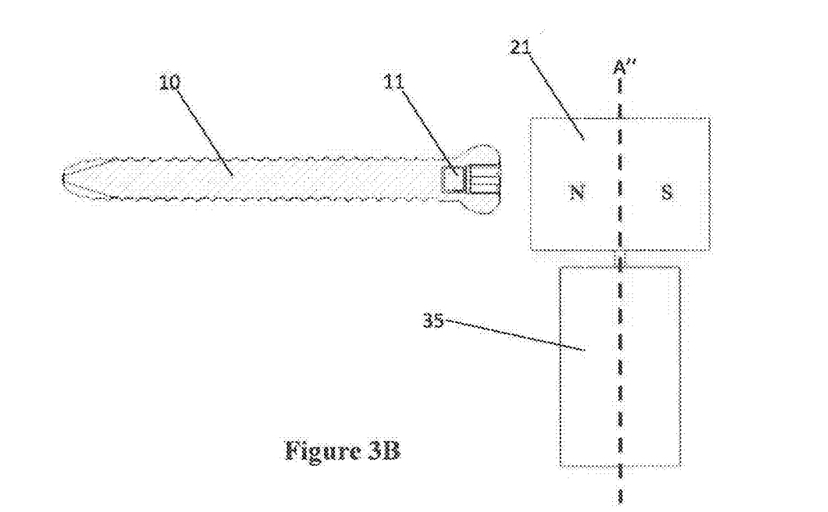
FIG. 3B: An external force generator in the form of a permanent magnet mounted to a motor output for imparting a dynamic force on a bone screw.

In another embodiment illustrated in FIG. 3A, an electromagnet is utilized in conjunction with drive electronics 23 to generate the dynamic magnetic field. When the force generator 20 is placed in the vicinity of bone screw 10, the magnetic field of electromagnet 30 and magnetic material 11 will interact, thereby generating force. The electromagnet could be cycled on/off to deliver dynamic force pulses to the bone, or various other dynamic arrangements. There may be benefits in delivering multiple force vectors to the bone area in need of repair. As such, alternating the direction of current flow 31 through electromagnet 30 could alternate. As current flow direction 31 alternates, north pole 32 and south pole 33 also alternate. The resulting force pulses would include force application in various opposing directions based on attractive and repelling interaction between the switching poles of the electromagnet 30 and the implantable element 10. Electromagnets suitable to penetrate subcutaneous tissue distances to impart forces on the implantable element tend to be expensive, large, and heavy. In another embodiment as illustrated in FIG. 3B, additional drive hardware in the form of an electric motor 35 is coupled to the permanent magnet 21 to impart motion. For example, drive motor 35 could be operably connected to permanent magnet 21 to rotate the magnet about axis A", thereby imparting a dynamic magnetic field on the adjacent magnetic material 11 included with the implantable element 10.

Figure 4A:
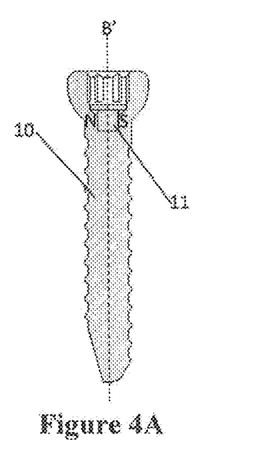
FIG. 4A: A section view of an implantable element including a permanent magnet.
Figure 4B:
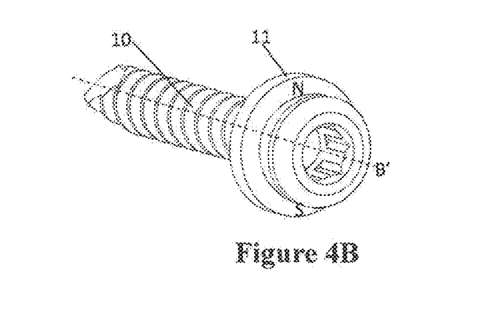
FIG. 4B: A perspective view of an implantable element including a permanent magnet.
Figure 5A:
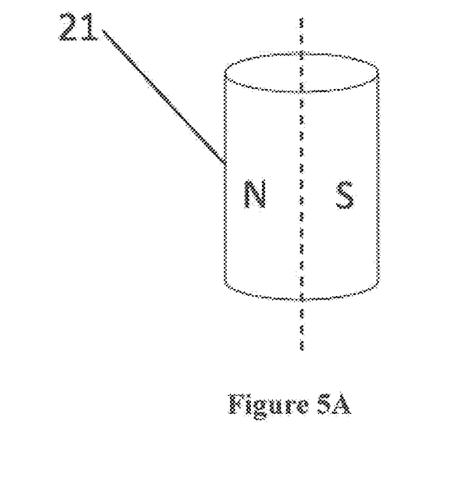
FIG. 5A: A diametrically magnetized permanent magnet for use in an external force generator.
Figure 5B:
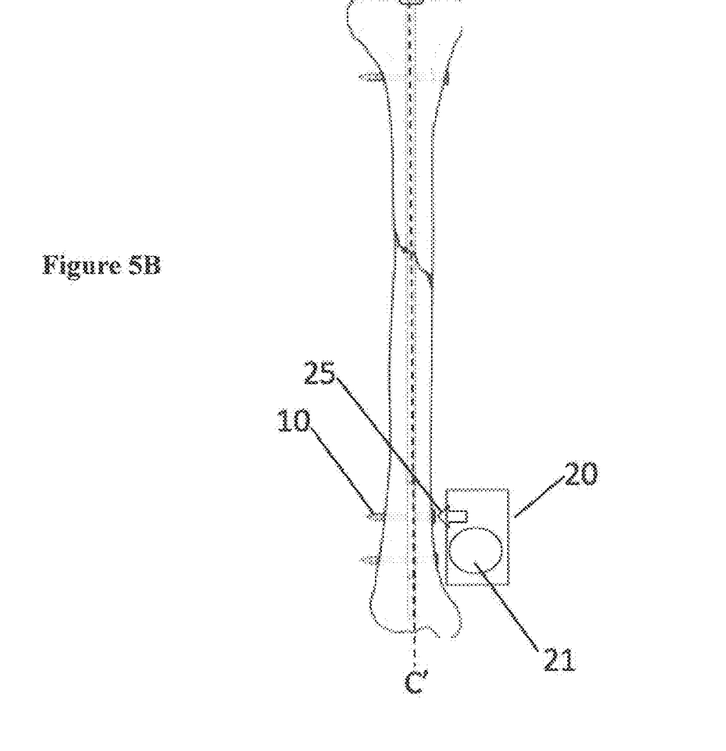
FIG. 5B: An anterior view of a tibia fracture in conjunction with the force delivery apparatus.
Figure 5C:
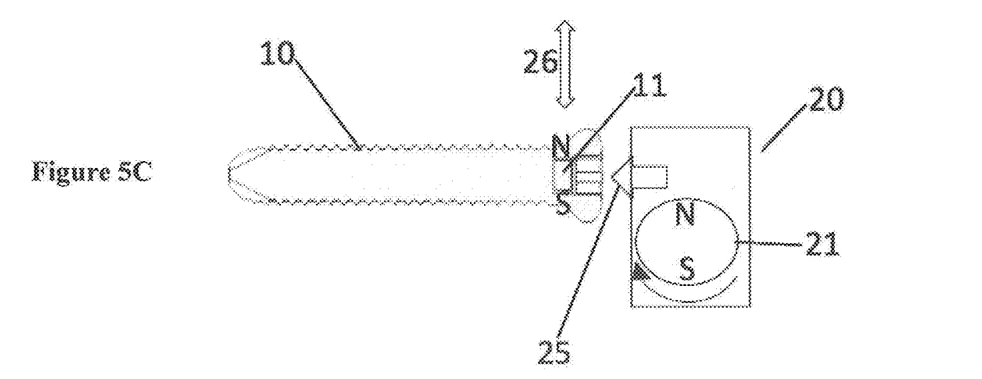
FIG. 5C: A detailed view of FIG. 5B illustrating the apparatus.
Figure 5D:
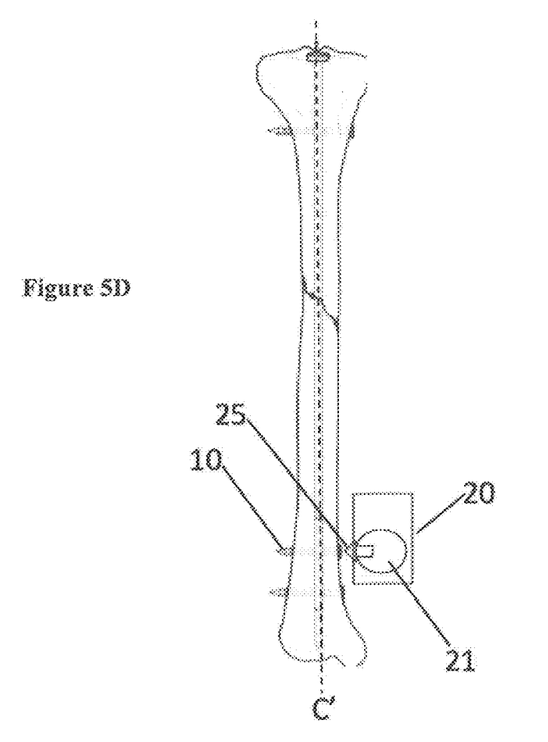
FIG. 5D: An anterior view of a tibia fracture in conjunction with the force delivery apparatus.
Figure 5E:
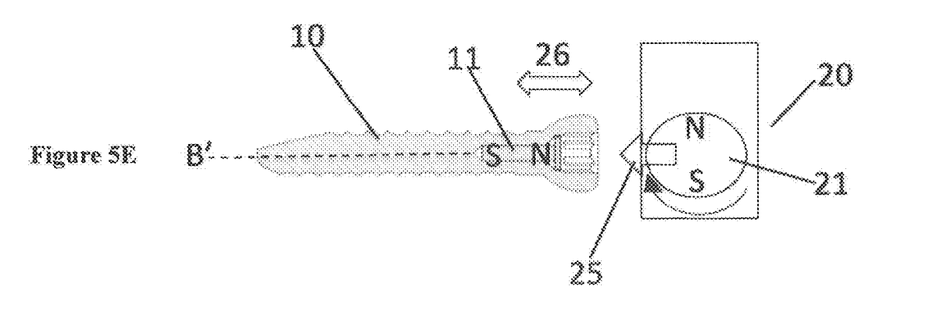
FIG. 5E: A detailed view of FIG. 5D illustrating the apparatus.

In delivering dynamic forces to a remote bone area in need of repair, the external force generator operates in cooperation with the implantable element to establish the magnitude and frequency of force application. A further inventive nature of the apparatus includes various provisions for controlling the direction of force application. FIG. 4A illustrates a bone screw 10 that includes a permanent magnet with poles oriented perpendicular to the screw axis B'. FIG. 4B illustrates another embodiment in which the bone screw 10 includes an alternative permanent magnet with its poles also oriented perpendicular to the screw axis B'. FIG. 5A illustrates a cylindrical permanent magnet 21 that is diametrically magnetized. In FIG. 5B, the diametrically magnetized permanent magnet 21 is operably mounted within the external force generator 20. The force generator 20 includes an alignment feature 25 that positions and orients the force generator with respect to the implantable element of the apparatus. In FIG. 5B, the implantable element is a bone screw 10. FIG. 5C is a detailed view of FIG. 5B illustrating the bone screw 10 with an embedded permanent magnet 11 whose poles are aligned substantially parallel with the axis of the tibia bone C'. The alignment feature 25 on the force generator 20 positions the rotating magnet 21 offset below the bone screw. In this orientation, the apparatus will deliver forces to the fracture site that are substantially in line with the axis of the tibia C' as indicated by force direction arrow 26. Such compressive forces at the fracture site have shown to be beneficial to the fracture healing process. In FIGS. 5D and 5E, the bone screw 10 has an embedded permanent magnet whose poles are aligned substantially parallel with the axis B' of the screw, and an external force generator 20 whose rotating permanent magnet 21 is aligned substantially coplanar with the screw. In this embodiment, the apparatus will deliver substantially shear type forces, as indicated by force direction arrow 26, to the fracture site. Shear forces at the fracture site are known to be less desirable, and even detrimental to stimulating bone repair at the fracture site. In these various inventive arrangements, the apparatus provides directionally controlled force delivery capabilities.

Figure 6:
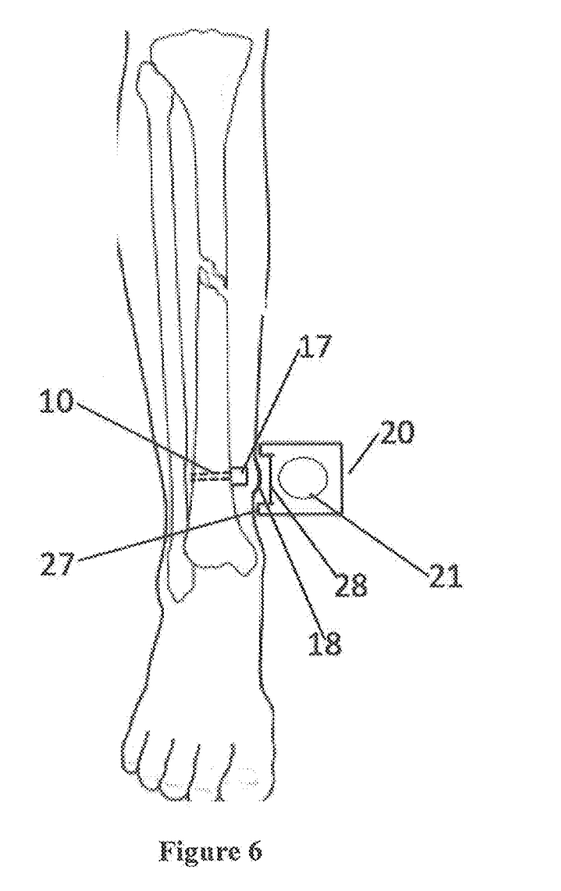
FIG. 6: An anterior view of a tibia fracture in conjunction with the force delivery apparatus.

FIG. 6 is another embodiment in which the implantable element 10 includes a feature, such as a screw head 17, positioned subcutaneous. Placing a portion of the implantable element in the subcutaneous space allows the implantable element to be easily located, for example by directly palpating the soft tissue 18. Successfully locating the implantable element allows for proper alignment and delivery of forces. Furthermore, the subcutaneous positioning minimizes the distance between the external force generator and the implantable element. Minimizing this distance is critical to accuracy of force delivery, overall cost of the apparatus, and patient safety. For example, a large separation distance between the implantable element and the external force generator would require a much stronger magnetic field. A stronger magnetic field can cost exponentially more to facilitate, presents inherent dangers for the patient, and reduces precision of force control. In the FIG. 6 embodiment, the external force generator 20 includes a mating receptacle 28 that engages and aligns over the screw head 17, thereby establishing the direction of force delivery. The external force generator may additionally include tissue compression features 27. The tissue compression feature 27 can further assist in aligning the external force generator 20 to the implantable element. Furthermore, the tissue compression feature(s) 27 compresses the soft tissue around the implantable element, thereby allowing the permanent magnet 21 to be positioned closer to the implantable element for more efficient and controlled force delivery.

Figure 7:
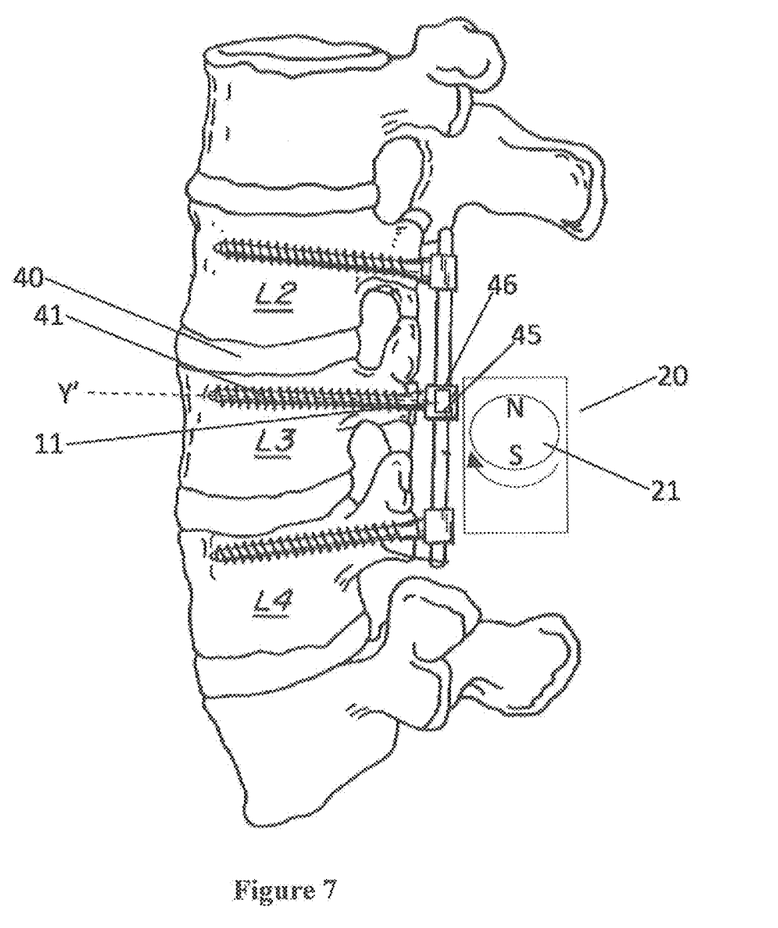
FIG. 7: A perspective view of the apparatus in conjunction with spinal fusion.

FIG. 7 illustrates a force delivery apparatus for delivering dynamic forces to a vertebral disc space to promote and accelerate spinal fusion. In spinal fusion procedures, the disc space 40 where the bone fusion is to occur is a remote location that would require significant risks and complexities to directly couple and apply force. FIG. 7 illustrates an embodiment in which forces can be transmitted into the disk space 40 by coupling with nearby generally healthy bone mass to transmit forces into the remote disc space 40. In the FIG. 7 embodiment, the implantable element is pedicle screw 41 that includes a permanent magnet 11 with north pole 45 and south pole 46 aligned vertically. The external force generator includes a rotating permanent magnet 21 located slightly offset below the pedicle screw's axis Y'. This arrangement emphasizes compressive forces on the disc space 40 to stimulate and accelerate the bone fusion. The FIG. 7 embodiment provides further illustrative example of the inventive nature in which the apparatus manages magnitude and direction of force delivery to a remote bone location.

Figure 8A:
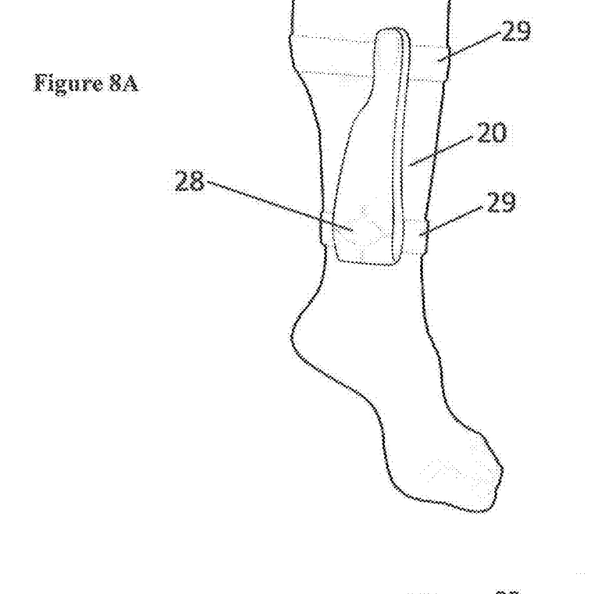
FIG. 8A: A perspective view of the apparatus in conjunction with a tibia fracture.

FIG. 8A illustrates a commercial embodiment of an external force generator 20 attached to a leg in a preferred orientation for delivering forces to a tibia fracture. The force generator 20 includes a mating receptacle 28 that engages and aligns over the implantable element. In this embodiment, alignment receptacles 28 are located on two opposing faces of the force generator, thereby making the apparatus ambidextrous for use on either left or right tibia. The external force generator includes straps 29 that attach the external force generator to the leg. The strap attachment provisions 29, along with the alignment receptacle 28, positions the apparatus for directional control of force delivery to the tibia fracture site.

Figure 8B:
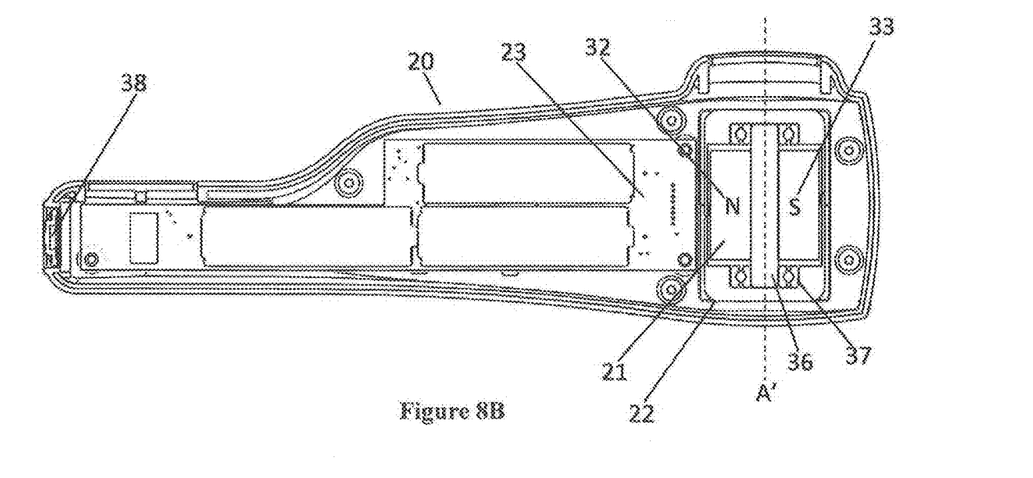
FIG. 8B: A perspective view of an external force generator.

FIG. 8B illustrates a commercial embodiment of an external force generator with one half of the enclosure open to illustrate the internal components. The apparatus includes a permanent magnet 21 that can rotate about axis A'. The permanent magnet 21 is a diametrically magnetized cylindrical magnet with north 32 and south 33 poles illustrated. The magnet 21 is operably mounted to shaft 36 and bearings 37. Winding 22 wraps around the permanent magnet 21, drive electronics 23 to energize and commutate the windings 22 to induce rotational magnet motion about axis A'. The permanent magnet 21 is operably mounted within the enclosure of the apparatus and between the alignment receptacles 28. The apparatus also includes an alignment LED 38. In this embodiment, the drive electronics 23 illuminate the LED 38 when the alignment receptacle 28 and permanent magnet 21 are in desirable position for force delivery with respect to the implantable element. This is accomplished through magnetic field strength sensors that are incorporated with the drive electronics 23. The drive electronics are also configured to establish the frequency of applied force, as well as duration. Research indicates bone cells can become oversaturated by stimulus within a short duration of 20 minutes or less. Additional stimulation beyond saturation point is not necessarily beneficial; therefore, the drive electronics automatically shut down the device after a prescribed amount of time. This avoids over stimulating the bone.

The invention claimed is:

1. An orthopedic device for delivering dynamic forces to a desired bone mass including a bone region in need of repair, the orthopedic device comprising:
   a plurality of implantable elements in the form of bone screws configured to be rigidly coupled to the desired bone mass, wherein a first implantable element of the plurality of implantable elements is configured to be coupled to a first side of the bone region in need of repair and a second implantable element of the plurality of implantable elements is configured to be coupled to a second opposite side of the bone region in need of repair, wherein the first implantable element comprises at least in part a magnetic material;
   a transfer element configured for operatively engaging with both the first implantable element and the second implantable element for transferring the dynamic forces from the first implantable element to the second implantable element; and a non-implantable external force generator configured for operative placement adjacent the first implantable element for interacting with the magnetic material of the first implantable element to generate dynamic forces that are transferred from the first implantable element to the second implantable element through the transfer element.

2. An orthopedic device according to claim 1, wherein said external force generator includes a permanent magnet configured to exhibit dynamic motion.

3. An orthopedic device according to claim 2, wherein the permanent magnet is configured to exhibit rotational movement.

4. An orthopedic device according to claim 1, wherein the magnetic material of the first implantable element is a permanent magnet.

5. An orthopedic device according to claim 1, wherein the second implantable element does not comprise a magnetic material.

6. An orthopedic device according to claim 1, wherein the first implantable element comprises a non-magnetic portion fully encapsulating the magnetic material, the magnetic material configured to be sealed with respect to an exterior of the first implantable element.

7. An orthopedic device according to claim 1, wherein the external force generator includes an electromagnet configured to be cycled on/off.

8. An orthopedic device according to claim 1, wherein the external force generator defines an enclosure enclosing a permanent magnet configured for rotation about an axis, a magnetic wire wrapped around the permanent magnet to create a winding, and drive electronics to energize and commutate the winding to induce rotational motion for the permanent magnet about the axis.

9. An orthopedic device according to claim 1, comprising an enclosure for operatively mounting components of the external force generator, the enclosure comprising features to align the enclosure with said first implantable element to operatively orient the direction of said dynamic forces applied to said first implantable element.

10. An orthopedic device according to claim 1, wherein the transfer element is an intramedullary rod.

11. An orthopedic device according to claim 1, wherein the transfer element is a bone plate.

12. An orthopedic device according to claim 1, wherein the transfer element is a vertebral fixation device.

13. An orthopedic device according to claim 1, wherein the orthopedic device is configured to deliver dynamic forces to long bones in a direction parallel with a longitudinal axis of the long bones.

14. An orthopedic device for delivering dynamic forces to a desired bone mass including a bone region in need of repair, the orthopedic device comprising:

a plurality of implantable elements configured to be rigidly coupled to the desired bone mass, wherein a first implantable element of the plurality of implantable elements is configured to be coupled to a first side of the bone region in need of repair, and a second implantable element of the plurality of implantable elements is configured to be coupled to a second opposite side of the bone region in need of repair, wherein the first implantable element comprises at least in part a magnetic material;

a transfer element configured for operatively engaging with both the first implantable element and the second implantable element for transferring the dynamic forces from the first implantable element to the second implantable element; and a non-implantable external force generator configured for operative placement adjacent the first implantable element for interacting with the magnetic material of the first implantable element to generate dynamic forces that are transferred from the first implantable element to the second implantable element through the transfer element, wherein the external force generator defines an enclosure enclosing a permanent magnet configured for rotation about an axis, a magnetic wire wrapped around the permanent magnet to create a winding, and drive electronics to energize and commutate the winding to induce rotational motion for the permanent magnet about the axis.

15. An orthopedic device for delivering dynamic forces to a desired bone mass including a bone region in need of repair, the orthopedic device comprising:

a plurality of implantable elements configured to be rigidly coupled to the desired bone mass, wherein a first implantable element of the plurality of implantable elements is configured to be coupled to a first side of the bone region in need of repair, and a second implantable element of the plurality of implantable elements is configured to be coupled to a second opposite side of the bone region in need of repair, wherein the first implantable element comprises at least in part a magnetic material;

a transfer element configured for operatively engaging with both the first implantable element and the second implantable element for transferring the dynamic forces from the first implantable element to the second implantable element; and a non-implantable external force generator configured for operative placement adjacent the first implantable element for interacting with the magnetic material of the first implantable element to generate dynamic forces that are transferred from the first implantable element to the second implantable element through the transfer element, wherein the orthopedic device further comprises an enclosure for operatively mounting components of the external force generator, the enclosure comprising features to align the enclosure with said first implantable element to operatively orient the direction of said dynamic forces applied to said first implantable element.

* * * * *